United States Patent [19]

Tamura

[11] 4,312,912
[45] Jan. 26, 1982

[54] PATIENT SUPPORTING TABLE TOP IN MEDICAL EXAMINATION AND THERAPY APPARATUS

[75] Inventor: Hisaaki Tamura, Otawara, Japan

[73] Assignee: Tokyo Shibaura Denki Kabushiki Kaisha, Japan

[21] Appl. No.: 135,660

[22] Filed: Mar. 31, 1980

[30] Foreign Application Priority Data

Apr. 2, 1979 [JP] Japan .................................. 54-41998

[51] Int. Cl.³ .......................... B32B 5/16; B32B 9/00; B32B 9/04; B32B 31/04
[52] U.S. Cl. .................................. 428/244; 156/148; 428/246; 428/283; 428/323; 428/402; 428/902
[58] Field of Search ........................... 250/439 R, 444; 428/306, 308, 402, 323, 244, 246, 283; 156/148

[56] References Cited

U.S. PATENT DOCUMENTS

| 3,515,625 | 6/1970 | Sedlak et al. | 428/308 |
| 3,707,434 | 12/1972 | Stayner | 428/308 |
| 3,897,345 | 7/1975 | Foster | 250/439 R |
| 4,134,019 | 1/1979 | Koontz et al. | 250/439 R |
| 4,146,793 | 3/1979 | Bergstrom et al. | 250/439 R |

Primary Examiner—William J. Van Balen
Attorney, Agent, or Firm—Finnegan, Henderson, Farabow, Dunner & Garrett

[57] ABSTRACT

A patient supporting table top for X-ray inspection apparatus which includes a platelike core member formed by mixing thermosetting resin with a great number of hollow carbon microspheres reinforced with carbon fibers and press-heating these materials. A covering member is bonded to each side of the core member by using an adhesive agent such as epoxy resin. The covering member is formed by mixing resin material with carbon fiber network and press-heating these materials.

5 Claims, 2 Drawing Figures

PATIENT SUPPORTING TABLE TOP IN MEDICAL EXAMINATION AND THERAPY APPARATUS

This invention relates to a table top used for supporting a patient in medical examination and therapy apparatus, such as X-ray diagnostic apparatus, X-ray therapeutic apparatus, medical nuclear apparatus, etc.

Figure 1:
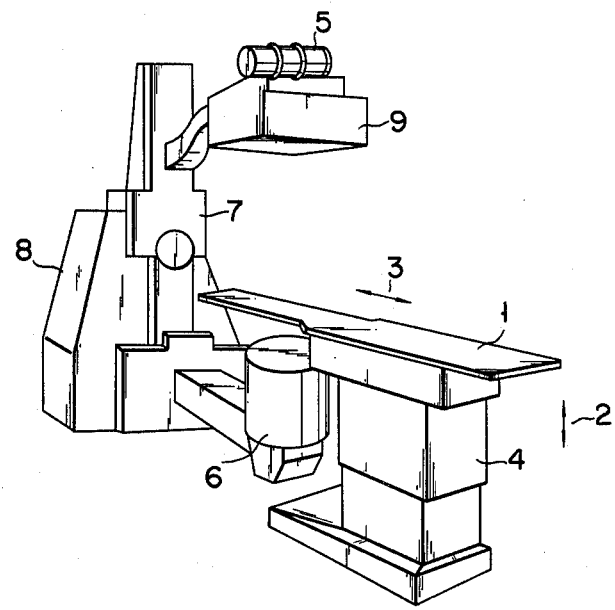

As an example of a medical apparatus of this type, FIG. 1 shows a prior art roentgenographic apparatus. In this apparatus, an elongated patient supporting top or table top 1 to bear a patient to be examined is disposed horizontally. There is a bedstead apparatus 4 which, supporting the table top 1, drives the same in the vertical direction indicated by arrow 2 and in the horizontal direction (along the longitudinal direction of the top) indicated by arrow 3. An X-ray tube device 5 and an image intensifier 6 are correspondingly disposed over and under the table top 1, respectively, so as to face each other with one end portion or forward end portion of the table top 1 in the form of a cantilever between. Both these devices are fixed on a rotating arm 7 so that they can rotate through an angle of 360° around the table top 1, accompanying the rotation of the arm 7. Numeral 8 designates a stationary stand supporting the arm 7. Numeral 9 designates an X-ray stop device disposed on the X-ray radiation side of the X-ray tube device 5, whereby the area of irradiation to the patient (not shown) on the table top 1 can be controlled. Further, the apparatus is so designed that X-ray films may be stored at the back of the image intensifier 6.

In such roentgenographic apparatus, the table top 1 is moved to be located so that a part to be irradiated of the patient on the table top 1 may be just on an X-ray radiation path. Then, X-rays radiated from the X-ray tube device 5 are applied to the patient through the X-ray stop device 9. Thereafter, the X-rays transmitted through the patient body are converted into an optical image by the image intensifier 6, and the image is photographed by using an X-ray film.

As essential properties for the table top 1 used with the above-mentioned apparatus, there may be enumerated, in the first place, minimized X-ray absorption to provide high-quality X-ray pictures, and considerable rigidity in the next. As regards the latter, it need be exhibited expressly along the longitudinal direction of the table top 1 because the table top 1 is slidden over a considerably long range, e.g. 1,500 mm or more, in the directions of arrows 3, having the elongated portion in the form of a cantilever, as shown in FIG. 1.

As a prior art table top to fulfill the aforesaid requirements, there is a table top which is formed of plywood or plastic plate whose cross-section is semilunar or crescent, in other words, in the form of a hollow wing. If formed of plywood, however, the table top of this type may be warped by temperature changes to become unfit for use. Also in the case of a table top formed of plastic, especially wetproof plastic, the rigidity is poor due to its low coefficient of elasticity, so that the flexure along the longitudinal direction of the table top is large, resulting in deterioration of the quality of X-ray pictures produced.

Disclosed in the specifications of U.S. Pat. Nos. 3,897,345 and 4,146,793 is a table top sharing the field with the table top of this invention in which foam material as a core member is covered with members formed of synthetic resin or carbon fibers. The sandwich-structure table top appearing in these specifications is a substantial improvement so far as the strength and X-ray permeability are concerned. Owing to external factors including temperature and humidity, however, even the table top of this structure cannot be a good solution to the problem of warping. The warping of the surface of the table top is a significant problem because it is impossible to perform satisfactory roentgenography for accurate X-ray diagnosis and treatment on an X-ray apparatus without accurately locating the region to be photographed.

In the conventional table top structure, the foam material of the core member suffers an unavoidable density variation as well as a nonuniform transmission of an X-ray or a gamma ray over the entire area, thus imparting an adverse influence to the quality of an image picked up. Moreover, the foam material is greater in its apparent density and it is impossible to obtain uniform transmission of the X-ray or gamma ray.

The object of this invention is to provide a patient supporting table top of high-rigidity structure eliminating the above-mentioned problems of the prior art table top and absorbing minimized quantity of X-rays.

In order to attain the above object, the patient supporting table top of this invention is formed by using independent hollow microspheres such as hollow carbon microspheres for the principal material of a core member, and fibrous material such as carbon fibers for the reinforcement of the core member. Covering members bonded respectively to both sides of the core member include a fiber network whose material is the same as that of said micropheres of the core member.

The "carbon hollow microsphere" appears, for example, in a monthly "Surface" Vol. 12 No. 2 pp. 93(27)-103(37) Feb. 1, 1974 Koshinsha Co., Ltd. U.S. Pat. No. 3,775,344 shows active carbon having a hollow microspherical structure.

According to this invention use can be made of such a hollow microsphere as disclosed in the above-mentioned references.

With the table top of this invention having such structure, since the principal material of the core member is the independent hollow microspheres, the apparent density or specific gravity is small, so that X-rays or gamma rays may be transmitted through the structure without being substantially absorbed thereby. Further, the composite-material structure of the core member provides high rigidity, eliminating the possibility of any substantial warping. Formed of similar materials, furthermore, the core and covering members have substantially the same coefficients of thermal expansion. In addition, the adhesive agent may be selected with ease, so that the fear of distortion attributable to changes in temperature or humidity, as well as the possibility of chemical changes, may be reduced.

Figure 2:
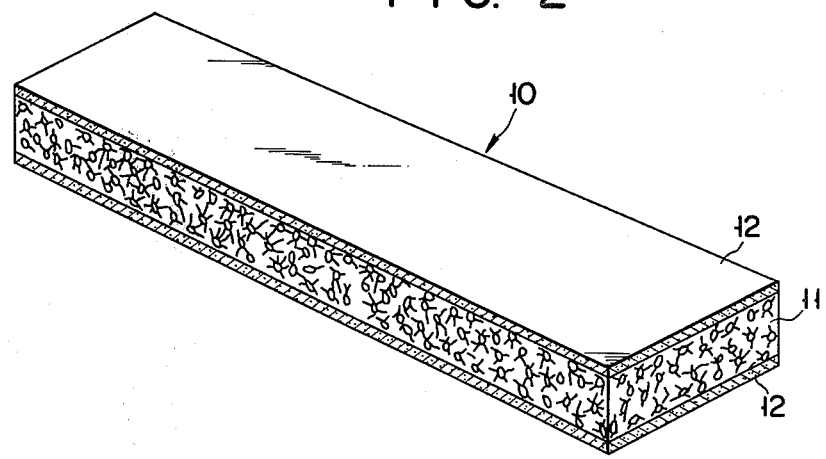

This invention can be more fully understood from the following detailed description when taken in conjunction with the accompanying drawings, in which:

FIG. 1 is a perspective view of a conventional roentgenographic apparatus using a patient supporting table top; and FIG. 2 is a perspective view of a patient supporting table top according to this invention partially in section along the crosswise and longitudinal directions.

Referring now to the drawing of FIG. 2, there will be described a preferred embodiment of a patient supporting table top of novel construction according to this invention.

In FIG. 2, the patient supporting table top 10 according to this invention, which may be used in place of the table top 1 shown in FIG. 1, is represented in a rectangular block for illustrating the internal structure.

The table top 10 is composed of a thick platelike core member 11 and thin covering members 12 bonded to the top and bottom of the core member 11.

The core member 11 is formed of a great number of hollow carbon microspheres as the principal material, carbon fibers as fibrous material for reinforcing the microspheres, and thermosetting resin, e.g. polyesters, mixed therewith. These materials are joined together by press-heating to form a plate.

As for the covering members 12, they include a fiber network whose material is the same as that of said microspheres of the core member 11, i.e. carbon fiber reinforced plastics, and further include resin material, such as epoxy resin, mixed with the fiber network. These materials are joined together by press-heating to form the flat or curved platelike covering members 12.

An epoxy resin adhesive may, for example, be used as the adhesive agent for bonding the covering members 12 to the top and bottom of the core member 11.

With the table top of the above-mentioned construction, the principal material of the core member 11 which constitutes the greater part of the thickness of the table top 10 is carbon of hollow microspheres, so that the apparent density or specific gravity is as small as e.g. 0.3 to 0.4 (g/cm$^3$). Accordingly, X-rays and gamma rays may be transmitted through the structure without being substantially absorbed thereby. Since both the core and covering members 11 and 12 are formed of composite materials, the table top as a whole can enjoy extremely high rigidity. Being of the same material or quality, moreover, the core and covering members 11 and 12 have substantially the same coefficients of thermal expansion, so that there is little chance of distortion due to changes in temperature or humidity. Furthermore, it is possible to properly select such adhesives as not suffering a chemical change.

Accordingly, where such table top of the invention is applied to a roentgenographic apparatus, for example, there will be obtained X-ray pictures of good quality to achieve the expected object of the invention, greatly contributing to the accuracy in diagnosis and therapy.

This invention is not limited to the abovementioned embodiment. Namely, the hollow microspheres constituting the core member are not limited to the hollow carbon microspheres. For example, they may be replaced by hollow glass or resin microspheres. If such different material is selected for the core member, the materials of the covering member should preferably be selected so that the covering member may have substantially the same properties including the coefficient of thermal expansion as those of the core member. Furthermore, it is necessary to select an optimum adhesive agent for the core and covering members according to the varied materials of these members.

The reinforcing fibrous material does not constitute a main material for the core member and can be neglected as required without losing the advantages of this invention. According to this invention, a greater number of hollow microspheres are important as the material of the core member.

What is claimed is:

1. A patient supporting table top for mechanical examination and therapy apparatus comprising a plate-like core member and covering layer members bonded to said core member, said core member being sandwiched between said covering layer members; the improvement wherein said core member includes a great number of independent hollow carbon microspheres as the principal material thereof, said microspheres being mixed with a thermosetting resin to form said core member, each said covering layer member including a carbon film network having a resin material mixed therewith to form carbon fibre reinforced plastic members.

2. A patient supporting table top according to claim 1, wherein said core member further includes fibrous material for reinforcing said microspheres.

3. A patient supporting table top according to claim 2, wherein said fibrous material of said core member is made of carbon.

4. A patient supporting table top according to claim 3, wherein an epoxy resin adhesive is used as an adhesive agent for bonding said core member with said covering layer members.

5. A method of manufacturing a patient supporting table top for medical examination and therapy apparatus, comprising the steps of forming a plate-like core member by mixing a thermosetting resin with a large number of independent hollow carbon microspheres, and then press-heating said mixed materials; forming covering layer members by knitting carbon fibres and mixing resin materials therewith, and then press-heating said mixed covering layer member materials; and bonding said covering layer members to each side of the core member using an adhesive agent.

* * * * *